| United States Patent [19] | [11] 3,941,453 |
| Kruger | [45] Mar. 2, 1976 |

[54] BIREFRINGENT COMPOUNDS USED IN KERR CELLS

[75] Inventor: Uwe Kruger, Hamburg-Schenefeld, Germany

[73] Assignee: U.S. Philips Corporation, New York, N.Y.

[22] Filed: Nov. 13, 1974

[21] Appl. No.: 523,329

[30] Foreign Application Priority Data

Nov. 15, 1973 Germany............................ 2357072

[52] U.S. Cl................................. 350/150; 252/300
[51] Int. Cl.$^2$........................................... G02F 1/07
[58] Field of Search ............. 350/150; 252/299, 300

[56] References Cited
UNITED STATES PATENTS 3,408,133  10/1968  Lee...................................... 350/150

*Primary Examiner*—Leland A. Sebastian
*Assistant Examiner*—David Leland
*Attorney, Agent, or Firm*—Frank R. Trifari; Norman N. Spain

[57] ABSTRACT

Molecules with a group X which attracts electrons and comprises $\pi$-electrons and conjugated therewith a group R which supplies electrons, of the formula $$R - X$$

in which X represents $-COCF_3$, $-COC_6H_5$ or $-SO_nCF_3$, $n$ being 0 or 2, and R represents phenyl or $(CH_3)_2N$, as electrooptically active liquid inter alia have the advantage that they are achromatic compared with nitrobenzene.

8 Claims, No Drawings

BIREFRINGENT COMPOUNDS USED IN KERR CELLS

The invention relates to a Kerr cell.

Kerr cells consist of two e.g. plate-shaped electrodes between which an electro-optically active liquid is disposed. In the normal condition, i.e. without electric field, the liquid is isotropic and does not influence the state of polarisation of a polarised light beam which traverses the Kerr capaciter. However, under the influence of an electric field set up between the electrodes the liquid will become optically uniaxially anisotropic (Internationale Elektronische Rundschau 21 (1967) 167).

Kerr cells are for example used in the switching stages of digital light deflectors to switch linearly polarised light from the direction of vibration of the incident light to a direction which is perpendicular thereto. When the light beam is polarised at 45° to the direction of the applied field, the plane of polarisation of the light beam will be rotated through 90° when the voltage $U_B$ between the electrodes has reached a certain value. By applying the voltages zero and $U_B$ respectively, it is possible to determine whether the beam in the following prism is subject to a refractive index $n_1$ or $n_2$ and accordingly leaves the prism in direction 1 or 2.

The combination of a Kerr-cell followed by a prism is referred to as deflection unit. By adding a second deflection unit whose prism has a refracting angle which is twice that of the first unit, the light beam can be deflected into four directions by actuation of the two Kerr-cell polarisation switches. By adding a third deflection unit with a prism having four times the original refracting angle, deflection into eight directions is possible. N deflection units enable $2^N$ directions. Said deflection system is of the digital type (Internationale Elektronische Rundschau, loc. cit.).

Until now only nitrobenzene was used as electro-optically active liquid in Kerr cells on account of its high Kerr constant. Nitrobenzene in the Kerr cells of e.g. digital light deflectors must be subjected to strong electric fields. These field strengths should allow of rapid and reproducible switching. Under the influence of the required electric field strengths of some $10^4$ V/cm nitrobenzene exhibits a substantial residual conductivity. Its resistance cannot be increased arbitrarily by even the most intensive purification. The residual currents, determined by polarisation and injection effects at the electrodes, lead to the formation of space-charge zones, which may distort or completely break down the field in the inter-electrode space. If electro-optically active liquids with substantially higher Kerr constants than that of nitrobenzene were available, this would allow the light deflectors to be operated with a correspondingly lower voltage. Thus, the disturbing effects might partially be avoided.

It is known that nematic substances in their liquid-crystalline phase exhibit a stronger Kerr effect than nitrobenzene (German Patent Application 2,234,522 which has been laid open for public inspection). The high degree of orientation in the electric field which is determined by the co-operative alignment of complete swarms of molecules, results in said strong Kerr effects.

On the other hand, said swarms of molecules require comparatively much time for alignment in the electric field. Therefore, with Kerr cell arrangements which employ nematic substances only low switching rates can be obtained (in the previously cited instance up to $2.10^5$ Hz). For multi-stage light deflectors, however, the Kerr cells should have switching frequencies of the order of magnitude of $10^8$ Hz. Theoretically, switching frequencies to within the range of $10^{10}$ Hz can be obtained only with substances whose Kerr effect is a property of the isolated molecules. With substances whose Kerr effect is not increased by molecular association, it is already extremely difficult to attain the Kerr-constant of nitrobenzene.

In view of the high switching frequencies, it is the object of the invention to provide a Kerr cell whose electro-optically active liquid consists of highly polar, optically strongly anisotropic and yet as small as possible molecules.

A further drawback of Kerr cells using nitrobenzene as electro-optically active liquid is that they must be comparatively thick in the direction of radiation (German Patent Application 2,234,522 which has been laid open for public inspection). Thicker layers of nitrobenzene are opaque to blue and violet light owing to their slightly yellow coloration. In order to enable the use of light deflectors in the entire visible and, if possible, also in the near ultraviolet spectrum, the invention also has for its object to provide a Kerr cell whose electro-optically actice liquid is moreover colourless.

In all, a suitable electro-optically active liquid should comply with the following requirements:
1. great dipole moment
2. high anisotropy of the optical polarisability
3. the main polarisability should coincide with the direction of the dipole moment
4. high dielectric constant
5. high number of active units per unit of volume - low molar volume.
6. short rotation relaxation time and low viscosity (to ensure sufficiently rapid alignment of the molecules in the field during rapid switching)
7. full transparency in the visible spectrum
8. the specific resistance of the material should be as high as possible.
9. The refractive index should as closely as possible approximate that of calcite, which is most frequently used for the prism ($n = 1.5–1.6$). The difference in refractive index should be minimized at the transition of the light from the electro-optically active liquid to the calcite prism.

The problem set fort hereinbefore is solved, according to the invention, by means of a Kerr cell which is characterized in that its electro-optically active liquid consists of molecules with a group X, which attracts electrons and comprises $\pi$-electrons, and conjugated therewith a group R, which supplies electrons, of the formula R — X, in which X = —COCF$_3$, —COC$_6$H$_5$ or —SO$_n$CF$_3$, $n$ being 0 or 2, and R = phenyl or (CH$_3$)$_2$N.

The compounds of the above formula are transparent to light to near-ultraviolet and have Kerr constants which are comparable with nitrobenzene.

Preferred embodiments of the Kerr cell according to the invention comprise at least one of the following compounds:

| name | graphic formula | Kerr constant (e.s.u., 20°C, 633 μ) |
|---|---|---|
| N,N-dimethyltrifluoro acetamide | $\begin{array}{c}CH_3\\ \phantom{x}\diagdown\\ \phantom{xx}N-C\\ \phantom{x}\diagup\phantom{xxx}\diagdown\\ CH_3\phantom{xxx}CF_3\end{array}$ with =O | $3.1 \cdot 10^{-5}$ |
| phenyltrifluoromethylsulphone | $CF_3$—$S(=O)(=O)$—phenyl | $2.7 \cdot 10^{-5}$ |
| N,N-dimethyltrifluoromethylsulphonamide | $\begin{array}{c}CH_3\\ \diagdown\\ N-S(=O)_2-CF_3\\ \diagup\\ CH_3\end{array}$ | $2.5 \cdot 10^{-5}$ |
| N,N-diethyltrifluoroacetamide | $\begin{array}{c}C_2H_5\\ \diagdown\\ N-C(=O)-CF_3\\ \diagup\\ C_2H_5\end{array}$ | $2.2 \cdot 10^{-5}$ |
| N,N-diethylbenzamide | $\begin{array}{c}C_2H_5\\ \diagdown\\ N-C(=O)-phenyl\\ \diagup\\ C_2H_5\end{array}$ | $1.9 \cdot 10^{-5}$ |
| phenyltrifluoromethylsulphide | $CF_3$—$S$—phenyl | $1.8 \cdot 10^{-5}$ |

(for comparison: nitrobenzene has a Kerr constant of $4.1 \cdot 10^{-5}$ e.s.u.).

The substances are chemically stable lowviscosity liquids. They can be purified satisfactorily. This is an essential requirement for their applicability as an electro-optically active liquid.

Compounds of the above-mentioned formulas are known per se. They may be prepared in accordance with known methods or methods analogous thereto.

The Kerr constants given in the above Table were measured during a high voltage pulse. Measurements of the field shape in nitrobenzene immediately after application of the voltage have revealed that the field is substantially undistorted in a substance of sufficient purity during the first few $10^{-4}$ seconds (Rev. gen. electr. (1965) 499; J.Chim. Phys. Physiochim. Biol. 65 (1968), 134). A measuring arrangement with pulsating field enables the actual Kerr constants of substances of average purity to be determined within this time interval. The Kerr constants determined for nitrobenzene of different purity with a stationary and with a pulsating external field differ substantially. The Kerr constants determined with a pulsating field are independent of the contamination of the nitrobenzene over the entire range.

The measurement of the Kerr constants of the compounds according to the invention with pulsating field was conducted with equipment as proposed by Lee (Ren. Sci. Instrum. 35 (1964), 1679) and also employed by Pearson (J. appl. Phys. 41 (1970), 2576) and Blanchet (in: High Speed Photography Proc. 8th Internat. Sympos., Stockholm 1968). The Kerr cells are disposed between two crossed polarizers, the plane of polarization of the incident light being selected so that it forms an angle of 45° with the direction of the external field. When subsequently an exponentially decreasing high voltage pulse is applied across the Kerr cell, the light intensity in the direction of observation passes through a sequence of maxima and minima. These are determined by the phase difference $\phi$ at decreasing voltage according to the equation (1) $\phi = 2 \pi\, l\, BE$ passing through a sequence of even and odd multiples of $\pi$. In this equation $l$ is the pathlength, B the volume Kerr constant (a material constant) and E the electric field strength. When $\phi$ corresponds to an odd multiple of $\pi$, this will result in maximum transmission in the case of the selected arrangement with the linearly polarised light being incident in the x-direction and the direction of observation being the y-direction. When $\phi$ equals odd multiples of $\pi$ the light vibrates parallel to and when $\phi$ equals even multiples of $\pi$ perpendicularly to the direction of transmission of the analyzer (in this case: direction of observation). The light intensity after the analyzer is given by (2) $I_y \sim I_{y(o)} \sin^2 (\phi/2) = I_{y(o)} \sin^2 (\pi\, BlE^2)$.

When, as is common practice, the lowest voltage at which light intensity a maximum occurs under the specified conditions is designated the $\lambda/2$ voltage.

(3) $U_{\lambda/2} = \dfrac{d}{\sqrt{2lB}}$ (for $\phi = \pi$ and $\lambda$ representing the wavelength of the incident light in vacuum) and when said equation is inserted in the relation (2), this yields $$(4) \quad I_v \sim I_{v(o)} \sin^2 \left( \frac{\pi}{2} \left( U \frac{U}{\lambda/2} \right)^2 \right).$$

The voltages at which further maxima are to be anticipated are consequently given by the relation $$U_{max} = U \lambda_{/2} \sqrt{2n+1}$$

and those for the further minima by $$U_{min} = U \lambda_{/2} \sqrt{2n, n}$$

$n$ being 0, 1, 2, . . . etc. Simultaneous monitoring on a double beam oscilloscope of the voltage drop across the Kerr cell and the transparency after the analyzer enables the voltages which correspond to the extreme values to be read directly. With the aid of equation (3) this yields the Kerr constant. As the voltage can only be measured with an accuracy of ± 50 V, the Kerr constants thus determined have an error which in the present examples varies between 5–10%. The pulse width is of the order of magnitude of 20–40 usecs., the maximum voltage 50 kV and the repetition frequency is 50 Hz. The Kerr constants of the substances examined were each time determined for several initial pulse voltages. Thus, the substances could be checked for sufficient preliminary purity in a simple manner. The $\lambda/2$ voltages of contaminated substances or substances which were unstable in the electric field are found to be increasingly excessive at an increasing initial pulse voltage. In contradistinction to this, the $\lambda/2$ voltages of sufficiently pure and stable substances are independent of the initial pulse voltage.

Thus, the invention provides Kerr cells with a series of colourless and chemically stable electro-optically active liquids, of which N,N-dimethyltrifluoroacetamide and phenyltrifluoromethylsulphone are the most active substances. Yet, their Kerr constants do not completely reach the value of nitrobenzene. However, when taking into account that the product of the volume Kerr constant and wavelength B. $\lambda$ is substantially constant and that thicker layers of the fluorinated amide are still fully transparent below 400 m $\mu$, it is evident that the slightly lower Kerr constant of the fluorinated amide need not be a drawback for its applicability as compared with nitrobenzene. N,N-dimethyltrifluoroacetamide exhibits the same Kerr effect at 380 m$\mu$ as nitrobenzene at 500 m$\mu$.

I claim:

1. A Kerr cell, characterized in that its electro-optically active liquid consists of molecules with a group X which attracts electrons and comprises $\pi$ -electrons and a group R which is conjugated therewith and supplies electrons, of the formula

R—X in which X = —COCF$_3$, —COC$_6$H$_5$ or —SO$_n$CF$_3$, $n$ being 0 or 2, and R = phenyl or (CH$_3$)$_2$N.

2. A Kerr cell as claimed in claim 1, characterized in that its electro-optically active liquid consists of N,N-dimethyltrifluoroacetamide.

3. A Kerr cell as claimed in claim 1, characterized in that its electro-optically active liquid consists of phenyltrifluoromethylsulphone.

4. A Kerr cell as claimed in claim 1, characterized in that its electro-optically active liquid consists of N,N-dimethyltrifluoromethylsulphonamide.

5. A Kerr cell as claimed in claim 1, characterized in that its electro-optically active liquid consists of N,N-diethyltrifluoroacetamide.

6. A Kerr cell as claimed in claim 1, characterized in that its electro-optically active liquid consists of N,N-diethylbenzamide.

7. A Kerr cell as claimed in claim 1, characterized in that its electro-optically active liquid consists of phenyltrifluoromethylsulphide.

8. A Kerr cell as claimed in claim 1, characterized in that its electro-optically active liquid consists of a mixture of at least two compounds of the formula R—X.

* * * * *